(12) United States Patent
Supper et al.

(10) Patent No.: US 7,651,500 B2
(45) Date of Patent: Jan. 26, 2010

(54) LIGAMENT TENSING DEVICE WITH DISPLACEABLE LUG

(75) Inventors: Walter Supper, Bettlach (CH); Christoph Fankhauser, Solothurn (CH); Beat Grunder, Worb (CH); Daniel Delfosse, Bern (CH); Ulrich Wehrli, Lugnorre (CH)

(73) Assignee: Mathys AG Bettlach, Bettlach (CH)

( * ) Notice: Subject to any disclaimer, the term of this patent is extended or adjusted under 35 U.S.C. 154(b) by 565 days.

(21) Appl. No.: 10/520,332

(22) PCT Filed: Jul. 1, 2003

(86) PCT No.: PCT/EP03/07012

§ 371 (c)(1),
(2), (4) Date: Sep. 14, 2005

(87) PCT Pub. No.: WO2004/004576

PCT Pub. Date: Jan. 15, 2004

(65) Prior Publication Data

US 2006/0155295 A1    Jul. 13, 2006

(30) Foreign Application Priority Data

Jul. 5, 2002 (DE) .............................. 102 30 375

(51) Int. Cl.
*A61B 17/60* (2006.01)
(52) U.S. Cl. .......................................... 606/90; 606/99
(58) Field of Classification Search ......... 606/86 R–88, 606/90, 96, 102
See application file for complete search history.

(56) References Cited

U.S. PATENT DOCUMENTS

| 5,020,519 | A | * | 6/1991 | Hayes et al. ................. 606/237 |
| 5,133,720 | A | * | 7/1992 | Greenberg .................... 606/96 |
| 5,213,112 | A | * | 5/1993 | Niwa et al. ................... 600/587 |
| 5,312,407 | A | | 5/1994 | Carter |
| 5,468,244 | A | | 11/1995 | Attfield et al. |
| 5,486,177 | A | * | 1/1996 | Mumme et al. ................ 606/79 |
| 5,536,271 | A | * | 7/1996 | Daly et al. .................... 606/80 |
| 5,630,820 | A | * | 5/1997 | Todd ............................ 606/90 |
| 5,669,914 | A | * | 9/1997 | Eckhoff ........................ 606/88 |
| 5,716,360 | A | * | 2/1998 | Baldwin et al. ............... 606/80 |
| 5,800,438 | A | * | 9/1998 | Tuke et al. .................... 606/90 |
| 5,941,884 | A | * | 8/1999 | Corvelli et al. ................ 606/88 |
| 5,944,723 | A | * | 8/1999 | Colleran et al. ............... 606/88 |
| 6,022,377 | A | * | 2/2000 | Nuelle et al. .................. 606/90 |
| 6,277,123 | B1 | * | 8/2001 | Maroney et al. ............. 606/102 |
| 2005/0256527 | A1 | * | 11/2005 | Delfosse et al. .............. 606/88 |

FOREIGN PATENT DOCUMENTS

WO    WO 00/78225 A1    12/2000

* cited by examiner

*Primary Examiner*—Thomas C Barrett
*Assistant Examiner*—Michael J Araj
(74) *Attorney, Agent, or Firm*—Scully, Scott, Murphy & Presser, P.C.

(57) ABSTRACT

A ligament tensing device (1) for activating a ligament and/or capsule system during implantation of a joint implant, comprising a base body (2) having a first lug (3) with a distal bearing surface (4) resting upon a first bone, and a second lug (7) resting upon a second bone with a proximal bearing surface (10) thereof. The second lug (7) is displaceable in an anterior-posterior and/or medial-lateral direction parallel to the first lug (3).

10 Claims, 1 Drawing Sheet

LIGAMENT TENSING DEVICE WITH DISPLACEABLE LUG

BACKGROUND OF THE INVENTION

1. Field of the Invention

The invention relates to a ligament-tensioning device for non-spheroid joints in the human or animal body.

2. Discussion of the Prior Art

A ligament-tensioning device for non-spheroid joints is known from WO 00/78225 A1. The device described therein for tensioning ligaments of non-spheroid joints in the human or animal body comprises a prismatic, cylindrical or plate-shaped base member having a right claw and a left claw, which comprise first bearing surfaces in a plane and may be brought to bear therewith in parallel against the joint-side surface of a first bone adjoining a non-spheroid joint. The ligament-tensioning device has a right handle and a left handle, a right tensioning lever and a left tensioning lever with second bearing surfaces, which are arranged parallel to the first bearing surfaces, wherein a tensioning width Y may be established between the respective bearing surfaces of the right tensioning lever and the right claw and the same or a different tensioning width X may be established between the respective bearing surfaces of the left tensioning lever and the left claw. The second bearing surfaces may be brought to bear against the joint-side surface of a second bone adjoining the joint. Moreover, the device comprises a right operating lever and a left operating lever, which may be actuated individually at the same time as the device is being held with one hand on each corresponding handle with the respective same hand, and a right parallel displacement device and a left parallel displacement device, which may each be driven by the corresponding operating lever and are each connected with a tensioning lever in such a way that, when the operating lever is moved, the tensioning widths X or Y respectively may be established independently of one another. The parallel displacement devices take the form of four-bar lever mechanisms.

A disadvantage of the ligament tensioning device known from WO 00/78225 A1 is in particular that the joint is in itself placed under tension after tensioning of the ligaments. The stresses lead to high frictional force between the ligament tensioning device and the bone resting thereon. This may result both in damage to the adjacent bone tissue during the course of the operation due to the friction and in sudden displacements of the ligament-tensioning device and/or of the bone due to ligament tension, which are uncontrollable and therefore disturb the course of the operation considerably.

SUMMARY OF THE INVENTION

The object of the invention is accordingly to provide a ligament tensioning device which makes it possible to tension the capsule-ligament structures of a joint to be provided with a prosthesis with a parallel spreading movement and at the same time to avoid transverse stresses with high frictional forces.

Advantageously, the second claw is of two-part construction, wherein the part facing the bone may be displaced relative to the part of the claw connected to the ligament tensioning device.

It is additionally advantageous for the movable part of the claw to be guided by means of a projection in a corresponding guide in the part of the claw connected with the ligament tensioning device.

A locking device, which may take the form for example of a tilting or rocking arm, advantageously ensures secure locking on introduction of the ligament-tensioning device and simple unlocking of the movable part of the claw after spreading apart.

Of particular advantage is the independent adjustability in the craniocaudal and anteroposterior directions. Displacement in the craniocaudal direction may for example be effected by means of a quantifiable parallel displacement device.

It is of further advantage that any desired rotational and translational degrees of freedom may be achieved, in order to be able to take account of the individual anatomical parameters of any particular (knee) joint.

BRIEF DESCRIPTION OF THE DRAWINGS

The invention is explained in more detail below with reference to schematic representations from different perspectives, in which.

DETAILED DESCRIPTION OF THE INVENTION

Figures 1, 2:
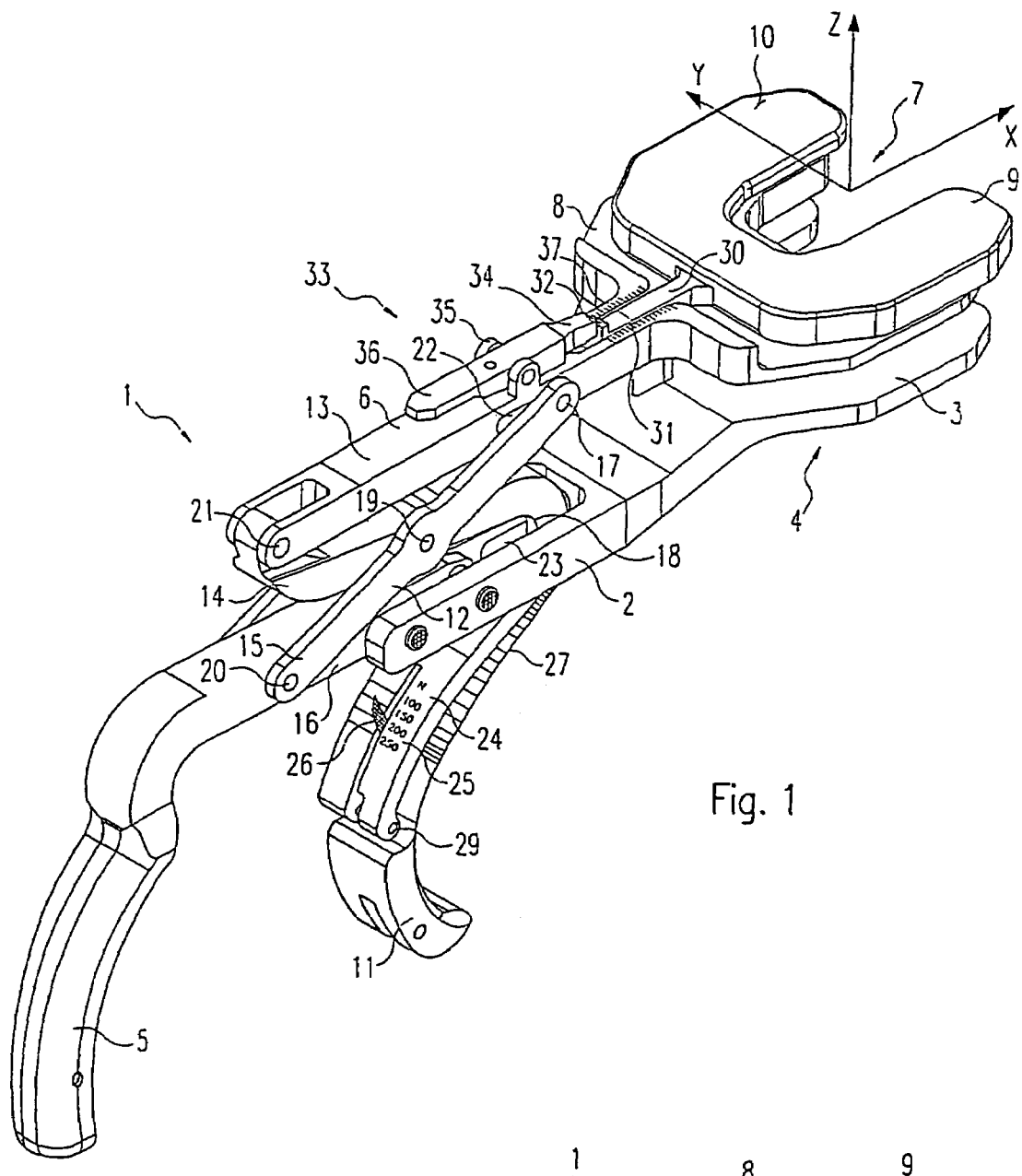
FIG. 1 is a schematic, perspective view of an exemplary embodiment of a ligament-tensioning device according to the invention.
FIG. 2 is a schematic plan view of the exemplary embodiment of a ligament-tensioning device according to the invention illustrated in FIG. 1.

FIG. 1 is a schematic, perspective overall representation of an exemplary embodiment of a ligament-tensioning device 1 configured according to the invention for a knee joint, in which displaceability of the claws relative to one another in the anteroposterior direction is achieved.

The ligament-tensioning device 1 comprises a base member 2, which, for reliable introduction of the spreading force into the tibia, has a first claw 3 with a distal bearing surface 4 relative to the knee joint gap, which bearing surface 4 rests on the tibia in the case of the knee joint. Opposite the first claw 3, a handle 5 is accordingly attached to the base member 2, which handle 5 allows the ligament-tensioning device 1 to be held and tensioned with one hand.

Likewise in accordance with the arrangement of the first claw 3 and located thereabove, the ligament-tensioning device 1 comprises a tensioning lever 6, on which a second claw 7 is arranged. According to the invention, the second claw 7 is of two-part construction. A first part 8 is connected to the tensioning lever 6, a second part 9 is arranged proximally, and displaceably, relative to the first part 8 with regard to the knee joint gap. The second part 9 comprises a proximal bearing surface 10, which bears on the opposite portion of the joint to be treated, i.e. the femur in the case of the knee joint. The spreading action is produced by actuating the handle 5 together with an operating lever 11.

With regard to the bearing surfaces 4 and 10, a parallel displacement device 12 allows parallel displacement of the second claw 7 with the bearing surface 10 relative to the first claw 3 with the bearing surface 4. During such displacement, the second claw 7 is in active connection with the tensioning lever 6. In the exemplary embodiment, the parallel displacement device 12 is constructed as a four-bar linkage in the form of intersecting rods and comprises four levers 13, 14, 15, 16, wherein a lever 13 on the tensioning lever side and a lever 16 on the base member side are arranged in parallel, while the levers 14 and 15 cross. The four levers 13, 14, 15, 16 are connected together by means of five axes 17, 18, 19, 20, 21.

Two of the axes 17, 18 are mounted in the parallel levers 13, 16 displaceably in grooves 22, 23 extending parallel to the bearing surfaces 4, 10.

This configuration of the parallel displacement device 12 allows the lever 13 on the tensioning lever side and the lever 16 on the base member side to move in parallel towards one another or away from one another. The lengths of the levers 13, 14, 15, 16 are so selected that, in the case of any desired tensioning width X between the bearing surface 4 on the first claw 3 and the bearing surface 10 on the second claw 7, which may be for example between 5 mm and 40 mm, a given conversion ratio prevails between the tensioning force applied manually to the handle 5 and the operating lever 11 and the distraction force exerted on the bones adjoining the joint.

The degree of spreading force may be read off from the force display 24 comprising a scale 25 and a movable display lever 26. The display lever 26 is moved by the longitudinal bending of the operating lever part 27 bendable by manually applied tensioning force relative to the other, display lever 26 arranged in the manner of a fork and not acted upon by this tensioning force. If the display lever 26 and the operating lever part 27 are moved relative to one another by means of the tensioning force, the display lever 26 turns around a pivot 29, whereby the manually applied tensioning force is displayed on the scale 25 by the display lever 26.

In addition, a locking device, not illustrated in any more detail in FIG. 1, may be provided between the handle 5 and the operating lever 11, which locking device allows the ligament-tensioning device 1 to be locked in a given position.

As already mentioned above, the second, proximal claw 7 is of two-part construction. The first, distal part 8 is connected to the tensioning lever 6 or is of one-piece construction therewith. The second, proximal part 9 is arranged on the first part 8 and may be shaped like a horseshoe, for example, in order to take account of the shape of the femur condyles, which bear thereon.

The proximal part 9 comprises a projection 30 which extends in the anteroposterior direction in a guide 31 formed in the lever 13. The projection comprises catches 32, into which a locking device 33, which in the exemplary embodiment is configured in the manner of a tilting arm or rocker, engages with an appropriately shaped extension 34. The locking device 33 pivots about an axis 35, which is disposed on the lever 13. A free end 36 of the locking device 33 serves in actuation of the locking device 33.

FIG. 2 is a schematic plan view of the exemplary embodiment illustrated in FIG. 1 of a ligament-tensioning device 1 according to the invention. Identical components are provided with matching reference numerals.

As already explained with regard to FIG. 1, the ligament-tensioning device 1 configured according to the invention comprises a proximal claw 7 which is at least partially displaceable relative to the distal claw 3 and on whose bearing surface 10 the femur condyles bear in the case of an operation on a knee joint.

In FIG. 2, the proximal part 9 of the second, proximal claw 7 is shown with the bearing surface 10 in the unlatched state. The catches 32 visible on the projection 30 are no longer in engagement with the extension 34 of the locking device 33.

The mode of operation of the ligament-tensioning device configured according to the invention is as follows:

If, during preparation for a knee joint implant, a device for tensioning the ligaments is introduced into the knee joint gap and spread apart by an amount X, forces acting obliquely, i.e. not in a craniocaudal or anteroposterior direction, may arise between the tensioning device and the bones bearing thereon due to superimposition of the stresses in ligaments and other soft tissue. These stresses, which may in principle act in any direction, may lead on the one hand, due to resultant frictional forces, to distortion of the quantifiable craniocaudal force and on the other hand to disturbances in the course of the operation, if for example the bones slip off the surface of the pretensioning device or stresses thereby dissipate jerkily or in an uncontrolled manner.

To prevent this, the ligament-tensioning device 1 configured according to the invention has a claw 7 arranged so as to be displaceable in the anteroposterior direction and movable relative to the other claw 3. The displaceable claw 7 is locked during introduction and spreading apart of the ligament-tensioning device 1 by means of the locking device 33 already described. Once the desired spreading force has been reached, the operator may release the locking device 33 by pressing on the end 36 thereof preferably with the thumb, such that the extension 34 is no longer engaged with the catches 32 of the projection 30. In this way, the proximal part 9 of the claw 7 slides in the posterior direction, pulled by the femur condyles bearing on the bearing surface 10 of the claw 7, until the knee joint is stress-free in this direction. In this way, no jerky stress dissipation can occur during the operation. In addition, the frictional force on the periosteum is reduced and the latter is thereby protected.

A scale 37 applied to the guide 31 allows quantification of anteroposterior displacement. This is useful, for example, for detecting the craniocaudal tensioning reaction and thus the influence of the rear cruciate ligament and other soft tissue systems on the relative displacement of the femur relative to the tibia and in addition for monitoring individual steps in soft tissue release. In addition, this quantification serves in objectifying experience gained from operations performed, whereby the knowledge collected therefrom may have an influence for the purpose of increased reproducibility in future operations.

It is advantageous to provide a corresponding apparatus also for the other translational and rotational degrees of freedom. For example, it is possible without difficulty to allow mediolateral movement by means of further guidance of the second part 9 of the proximal claw 7. Rotational degrees of freedom, which allow rotation about various axes, are also feasible. Spheroid joint connections between the claws 3 and 7 and the ligament-tensioning device 1 would, for example, allow tilting of the claws 3 and 7 relative to one another and could be freely inserted into the exemplary embodiment described. The advantages of such extensions are, in particular, problem-free adaptation to individual anatomical parameters of any particular (knee) joint and easy spreading apart of the device for quantifying the actual craniocaudal reaction forces.

The invention claimed is:

1. A ligament-tensioning device for activating the ligament and/or capsule apparatus during implantation of a joint implant, having a base member comprising a first claw with a distal bearing surface, which is adapted to bear on a first bone, and a second claw, which is adapted to bear with a proximal bearing surface on a second bone, wherein the second claw is of a two-part construction having a distal part and a proximal part, wherein the distal part is displaceable relative to the proximal part to enable displacement of the second claw in an anteroposterior direction and/or mediolateral direction parallel to the first claw, wherein displacement of the second claw in a craniocaudal direction is enabled by a parallel displacement device, a projection comprising catches that are formed on the proximal part of the second claw being guided in a guide, a locking device being movably engageable in the catches, and the locking device possessing the form of a tilting or rocking arm which is pivotable about an axis.

2. A ligament-tensioning device for activating the ligament and/or capsule apparatus during implantation of a joint implant, having a base member comprising a first claw with a distal bearing surface, which is adapted to bear on a first bone, and a second claw, which is adapted to bear with a proximal bearing surface on a second bone, wherein the second claw is of a two-part construction having a distal part and a proximal part, wherein the distal part is displaceable relative to the proximal part to enable displacement of the second claw in an anteroposterior direction and/or mediolateral direction parallel to the first claw, and wherein displacement of the second claw in a craniocaudal direction is enabled by a parallel displacement device, a projection comprising catches that arc formed on the proximal part of the second claw is guided in a guide, a locking device being provided on the second claw, and the proximal part of the second claw being releasable relative to the distal part of the second claw by actuation of the locking device.

3. A ligament-tensioning device according to claim 2, wherein the locking device engages movably in the catches.

4. A ligament-tensioning device according to claim 1 or 2, wherein the guide comprises a scale.

5. A ligament-tensioning device according to claim 1 or 2, wherein said locking device is provided on the second claw.

6. A ligament-tensioning device according to claim 1 or 2, wherein the first claw and the second claw are displaceable parallel to one another in the craniocaudal direction by means of the parallel displacement device.

7. A ligament-tensioning device according to claim 6, wherein the ligament-tensioning device comprises a force display for the force applied in the craniocaudal direction by the parallel displacement device.

8. A ligament-tensioning device according to claim 7, wherein the anteroposterior and/or mediolateral displacement of the first claw and the second claw relative to one another is effectable independently of the craniocaudal displacement of the first claw and the second claw relative to one another.

9. A ligament-tensioning device according to claim 1 or 2, wherein the second claw is arranged in such a way that rotation of the second claw relative to the first claw is effectable in a varus-valgus direction, in an internal-external direction and in a flexion-extension direction.

10. A ligament-tensioning device according to claim 9, wherein the rotations in the varus-valgus direction, in the internal-external direction and in the flexion-extension direction are effectable independently of one another.

\* \* \* \* \*